United States Patent [19]
Karol et al.

[11] 4,208,399
[45] Jun. 17, 1980

[54] TOLYL ISOCYANATE TEST ANTIGENS, METHODS FOR THEIR PREPARATION AND USE IN DETECTING DIISOCYANATES AND ANTIBODIES TO DIISOCYANATES

[75] Inventors: Meryl H. Karol; Yves C. Alarie, both of Pittsburgh, Pa.

[73] Assignee: The University of Pittsburgh, Pittsburgh, Pa.

[21] Appl. No.: 934,023

[22] Filed: Aug. 16, 1978

[51] Int. Cl.² .................... G01N 33/16; A61K 43/00; C07G 7/00
[52] U.S. Cl. ...................................... 424/1; 23/230 B; 424/12; 260/112 B
[58] Field of Search .................. 424/1.5, 1, 12; 23/230 B; 260/112 B

[56] References Cited

U.S. PATENT DOCUMENTS

| | | | |
|---|---|---|---|
| 3,443,903 | 5/1969 | Haack | 23/230 B |
| 3,549,328 | 12/1970 | Kilburn | 23/230 B |
| 3,838,012 | 9/1974 | Higgins | 23/230 B |
| 4,031,197 | 6/1977 | Marinkovich | 424/1 |

Primary Examiner—Richard E. Schafer
Assistant Examiner—Christine M. Nucker
Attorney, Agent, or Firm—Buell, Blenko & Ziesenheim

[57] ABSTRACT

An antigen and a method for its preparation and use in detecting antibody to a selected diisocyanate is provided by reacting the monoisocyanate derivative of the diisocyanate with a protein, incubating the antigen on a paper disc with test serum in the presence of a buffer and anti-IgE-$^{125}$I and thereafter counting the disc in a scintillation fluid with a liquid scintillation spectrometer.

12 Claims, 1 Drawing Figure

Figure 1 -- PRIST assay for tolyl-specific IgE in sera from workers exposed to TDI and from Blood donors. Connected points indicate titers of sera taken one month apart from the same individual. Net cpm = cpm (TMI-HSA discs) - cpm (HSA discs).

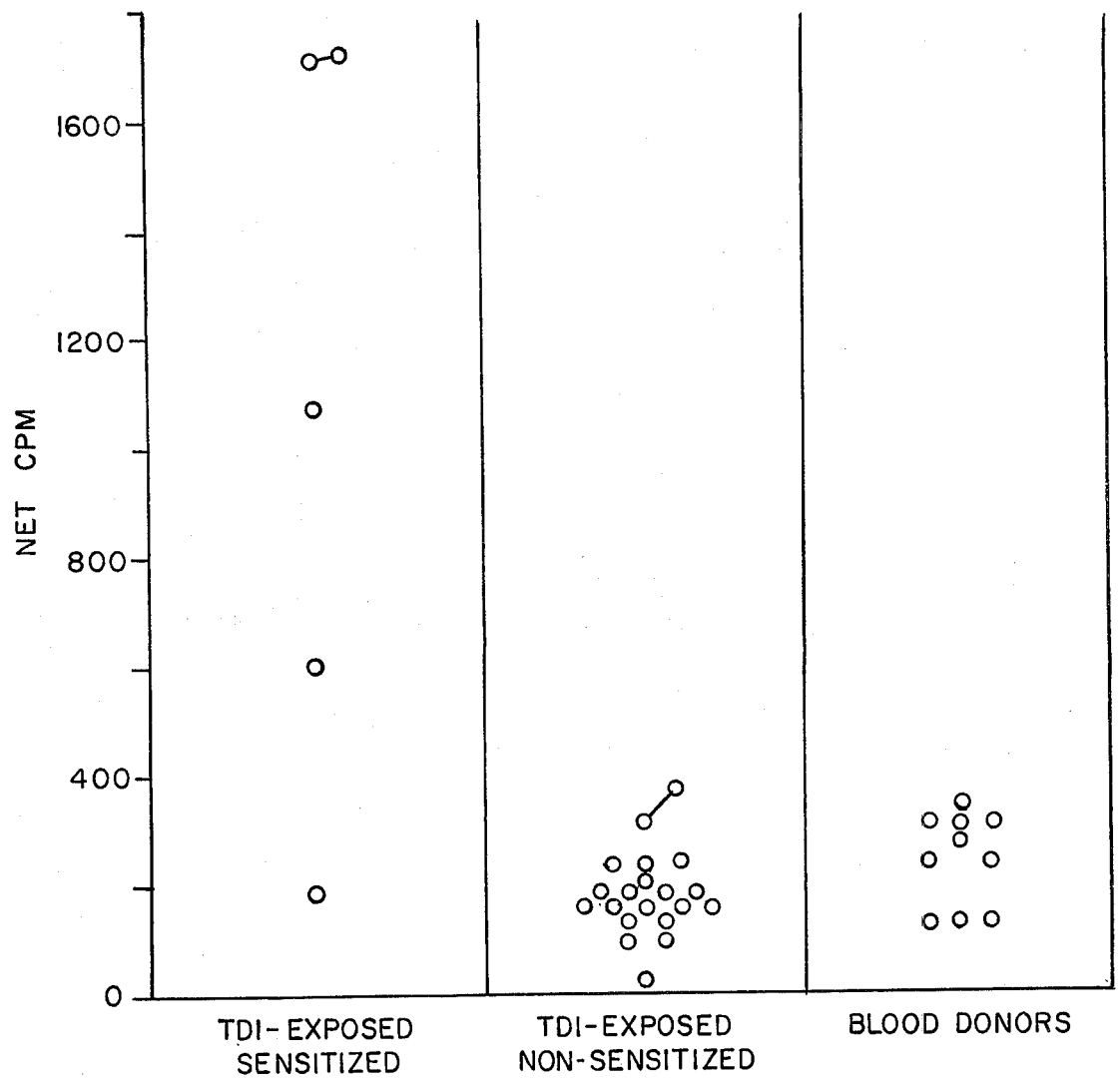
Figure 1 -- PRIST assay for tolyl-specific IgE in sera from workers exposed to TDI and from Blood donors. Connected points indicate titers of sera taken one month apart from the same individual. Net cpm = cpm (TMI-HSA discs) - cpm (HSA discs).

TOLYL ISOCYANATE TEST ANTIGENS, METHODS FOR THEIR PREPARATION AND USE IN DETECTING DIISOCYANATES AND ANTIBODIES TO DIISOCYANATES

This invention resulted from work done under Contract No. ROI-ES01532 with the National Institute of Environmental Health Science of the Department of Health, Education and Welfare, and is subject to the terms and conditions of the Presidents Patent Policy Statement of Oct. 10, 1963.

This invention relates to tolyl isocyanate test antigens, methods for their preparation and use in detecting diisocyanates and antibodies to diisocyanates and particularly to a tolyl isocyanate test antigen for the detection of hypersensitivity antibodies to toluene diisocyanate and other diisocyanates in workers.

Diisocyanates and particularly toluene diisocyanate (TDI) are highly reactive chemicals used in the manufacture of plastics, foams and paints. They are the basic ingredients in the group of plastics known as urethanes which are used in the manufacture of insulation cushioning material, building panels, food containers and a vast array of goods. TDI in particular has been cited frequently as a potent sensitizer in the industrial environment, possibly because it is such a heavily used item. However, other industrial diisocyanates such as hexamethylene diisocyanate, methylene diisocyanate, isophorone diisocyanate and naphthylene diisocyanate find sustantial use in industry and pose a like problem of hypersensitivity. It is generally recognized that about 5% of those persons exposed to TDI become sensitized and suffer asthmatic reactions upon subsequent exposure to even extremely low concentrations of the chemical. A great deal of work has been done in an effort to find a specific test for the presence of this sensitivity and specifically for TDI specific antibodies through which some measure of sensitivity might be established. This past work has failed to produce any satisfactory test or mechanism for detecting anti-TDI antibodies. The difficulty in detecting anti-TDI antibodies may result from the chemical reactivity of TDI. The known tendency of TDI to cross-link protein molecules apparently precludes preparation of hapten-conjugated test antigens which contain exposed tolyl groups. In any event a satisfactory test technique has evaded prior attempts at solution.

We have discovered that a test antigen for TDI can be prepared from the monoisocyanate derivative of toluene in place of TDI itself. Similarly test antigens of other industrial diisocyanates can be prepared from the corresponding monoisocyanate analogues and these monoisocyanate analogues are suitable for detecting the diisocyanates and antibodies thereof. Since the TDI detection is by far the most important due to the large tonnages of TDI used in industry and the corresponding greater exposure we shall illustrate the preparation of monoisocyanate antigen for induction of tolyl specific serum antibodies in mammals.

The invention can accordingly be best understood from the test examples set out hereafter and from the drawings in which the single FIGURE is a graph of PRIST radioimmunoassay for a group of test sera.

Test Subjects

Twenty-three employees of a large TDI production facility were chosen as test subjects. At the time of this test all subjects had been employed at TDI production facility for at least one year. Four of the employees were considered to be sensitive to TDI; 3 of these 4 had experienced a hypersensitivity response (either pulmonary or cutaneous) within one year prior to the study, the fourth individual had taken precaution to avoid exposure to TDI for at least two years prior to study. The remaining 19 employees were not considered to be sensitive to TDI. This conclusion was based on inhalation challenge studies using 0.02 ppm TDI or complete absence of adverse reactions upon TDI exposure. Sera were evaluated using a blind study. Identities of the donors were made known only after completion of all serological determinations. The study also included sera from ten adult healthy blood bank donors.

The test thus involved 23 persons employed at a TDI facility and 10 randomly selected persons for a total of 33 subjects.

The Test Antigen

A test antigen containing p-tolyl isocyanate and human serum albumin (HSA) was prepared as follows: 280 μl p-tolyl isocyanate (Eastman Organic Chemicals) was added to a chilled, rapidly stirred, 1% solution of HSA (Sigma Chemical Co.) in borate buffer at pH 9.4. Following extensive dialysis, spectroscopic examination of the conjugate indicated an average substitution of 10 moles of hapten per mole HSA. This antigen formulation follows the pattern:

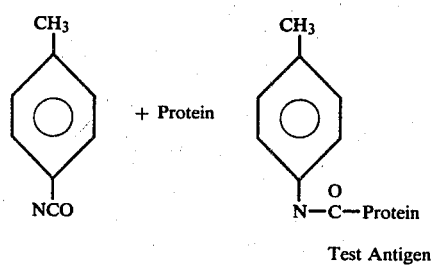

Test Antigen

The corresponding formulations for antigens of the monoisocyanate analogues of other industrial diisocyanates is typified by the following equations:

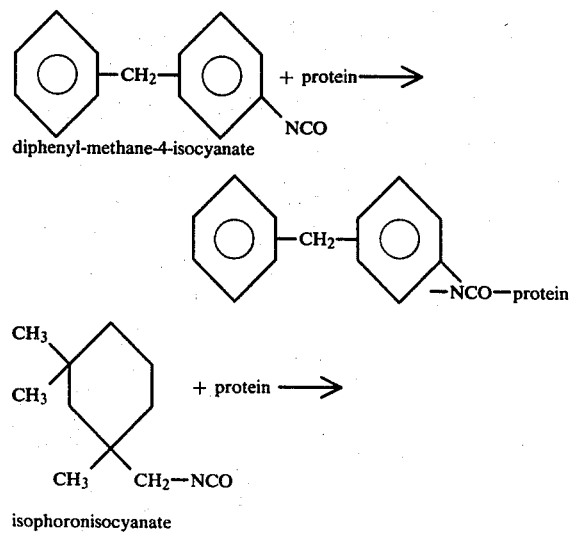

diphenyl-methane-4-isocyanate isophoronisocyanate

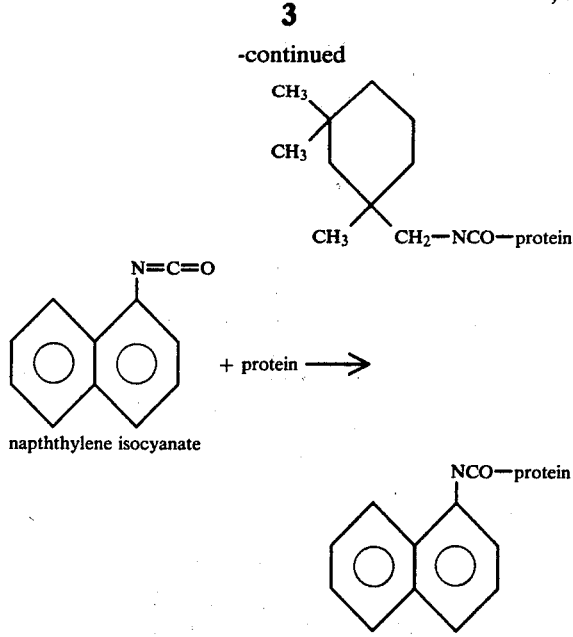

Radioimmunoassay for anti-tolyl antibodies

A PRIST (Paper Radioimmunosorbent Test) was developed using the TMI-HSA antigen bound to 5 mm paper discs (Whatman #44), the latter previously activated with cyanogen bromide. For coupling, 4 ml antigen (20 mg/ml) in 0.1 M NaHCO$_3$ was added to 100 mg activated discs and the mixture was incubated on a rotator at ambient temperature for 6 hours. Discs were then washed 3 times with 0.1 M monoethanolamine in 0.1 M NaHCO$_3$ and stored in this solution overnight at 10° C. The following day, discs were washed 3 times with incubation buffer (0.05 M phosphate, pH 7.4, 0.85% NaCl, 1.0% bovine serum albumin, 0.05% NaN$_3$). For the test, 100 μl serum was added to a tube containing an antigen-coated disc and incubated overnight on a rotator at ambient temperature. Discs were then washed 3 times with 0.85% NaCl-1% Tween 20 (S-T) before incubation with 100 μl anti-IgE-$^{125}$I (Phadebas Rast reagent, Pharmacia Diagnostics 1977). The latter reagent is specific for the D$_{\epsilon 2}$ determinant of human IgE. Following overnight incubation, discs were again washed 3 times with S-T then counted in 10 ml ACS scintillation fluid (Amersham Searle Corporation) using the tritium channel on a Packard Tri-Carb liquid scintillation spectrometer. All sera were processed in duplicate. IgE antibody reactive with tolyl groups was determined from the activity bound to TMI-HSA-coated discs compared with activity bound to HSA-coated discs. The latter values were obtained from separate incubation of serum samples with paper discs reacted with HSA alone. The correction ranged between 100-150 counts per minute. Tolyl-specificity of IgE antibodies was also indicated by hapten inhibition studies as detailed below.

Hapten inhibition of serum binding

Tolyl-specificity of IgE antibody binding to TMI-HSA paper discs was additionally measured by hapten inhibition. Haptens used were toluene 2,4 diamine and a conjugate of p-tolyl isocyanate and ε-aminocaproic acid. Synthesis of the conjugate hapten was carried out by dropwise addition of p-tolyl isocyanate and ε-aminocaproic acid to a chilled 1% solution (w/v) of ovalbumin (Sigma, Grade V) in 0.05 M boric acid-0.5 M KCl-0.035 M NaOH buffer, pH 9.4. The synthesis employed equimolar amounts of the two reactants. The reaction mixture was stirred at 0° C. for 30 minutes and then centrifuged. The supernatant was allowed to react an additional 60 minutes, then dialyzed against saline for 24 hours, then against distilled water for 72 hours. The product was isolated by acidification of the reaction mixture to pH 4.5. Following purification of p-tolylureido caproate by repeated acid-base precipitation and dissolution, it was recrystallized from hot ethanol $\epsilon_{242\ nm}=11,400$, mp=135° C. The extent of "tolyl" substitution of tolyl ovalbumin was determined from the 242 nm absorbance in excess of that due to ovalbumin. To demonstrate inhibition, TMI-HSA coated discs were incubated with test serum (100 μl) in the presence of hapten dissolved in 50 μl normal horse serum (Pharmacia Diagnostics). Following a 24 hour incubation, IgE binding to the discs was evaluated using anti-IgE-$^{125}$I as described above. Inhibition was determined by comparison of the binding of the test serum in the presence and absence of inhibitor.

Total IgE

The Phadebas IgE PRIST test kit (Pharmacia Diagnostics) was used to determine total IgE in sera. Values were converted to IgE Units/ml by comparison with a standard serum supplied by the manufacturer.

RESULTS

Tolyl-specific IgE

Results of the PRIST radioimmunoassay for IgE antibody bound to TMI-HSA discs are presented as net counts per minute (cpm) in the accompanying FIGURE and Table I. The group of 19 TDI-exposed, non-sensitized workers had antibody titers comparable to those found in sera from blood bank donors. The TDI-sensitized group, on the other hand, displayed markedly elevated titers of anti-tolyl antibody. The geometric mean titer of the latter group of sera differed significantly from that of the non-sensitized workers (99% confidence level, t test with unequal variance). Within the TDI-sensitized group, the only serum lacking a significant antibody titer (P<0.05) was from the individual unexposed to TDI for at least two years prior to this study. Each of the other three TDI-sensitive persons had significant titers. In two cases, it was possible to obtain second serum samples one month following the initial sample. The first and second determinations from individual workers are indicated with a connecting line in the FIGURE.

Tolyl-specificity of IgE binding to TMI-HSA discs was demonstrated by hapten inhibition. In the presence of 500 ug p-tolyl ureido caproate in one case, and 250 L ug toluene, 2,4 diamine in another case, 50% and 48% less antibody became bound to the TMI-HSA discs, respectively. The same quantities of hapten had no inhibitory effect in control IgE-anti-IgE-$^{125}$I PRIST systems.

Total IgE Concentrations

To determine if the tolyl-reactive IgE antibodies identified in sera from TDI-sensitized persons merely reflected high levels of IgE in the serum, total serum IgE was measured. The results, shown in Table I, indicate no apparent relationship between tolyl-directed IgE antibodies and the amount of IgE in sera. Cases #1,

4, and #15, each with significant titers of tolyl-specific IgE antibody, did not have unusually high amounts of total IgE. Moreover, the elevated levels of IgE seen in cases #3, #6, and #8, did not correlate with increased levels of tolyl-specific IgE antibody.

TABLE I

Total IgE and Tolyl-Specific IgE in Workers Exposed to Toluene Diisocyanate (TDI)

| Case | Total IgE* (Units/ml) | Tolyl-Specific IgE (net cpm) |
|---|---|---|
| +1 | 42 | 1714 |
| 2 | 71 | 154 |
| 3 | 90 | 247 |
| +4 | 36 | 598 |
| 5 | 25 | 179 |
| 6 | >100 | 311 |
| 7 | 22 | 150 |
| 8 | 95 | 240 |
| 9 | <1 | 115 |
| 10 | 9 | 160 |
| 11 | 84 | 230 |
| 12 | 3 | 151 |
| 13 | 84 | 128 |
| 14 | 34 | 195 |
| +15 | 10 | 1077 |
| 16 | 65 | 18 |
| 17 | 44 | 82 |
| 18 | 4 | 99 |
| 19 | 54 | 142 |
| 20 | 82 | 210 |
| ++21 | 56 | 187 |
| 22 | 11 | 199 |
| 23 | 86 | 173 |

*Geometric mean value for normal adults is 14 Units/ml.
+ Workers with clinical evidence of sensitivity to TDI.
++ Worker unexposed to TDI for >2 years prior to this study.

The foregoing test results are directed toward identification of the IgE class of antibody in workers displaying clinical TDI hypersensitivity. The titers of tolyl-IgE antibody found in sera from TDI-exposed, non-sensitive workers were indistinguishable from antibody levels found in the normal adult population studied. It is apparent, therefore, that the presence of tolyl-specific IgE antibodies is not solely a reflection of TDI exposure. The occurrence of specific IgE antibodies only in those workers with hypersensitivity to the isocyanate implies a causal role for these antibodies.

Tolyl-specific IgE antobidies were detected in 3 of the 4 sensitized workers. The highest titer (case #1) was found in a person with acute pulmonary hypersensitivity to TDI. This person responded to bronchial challenge with 0.006 ppm TDI. Cases #4 and #15 display immediate skin reactions upon exposure to TDI. This skin sensitivity was not of the irritant type since the affected areas were extensive and not confined to regions where TDI contacts the skin. Allergic eczema to TDI has been reported although most reports of TDI hypersensitivity pertain to the bronchial response. The fourth case (#21) of TDI-hypersensitivity had not been exposed to TDI for at least two years prior to this study. Failure to detect tolyl-specific antibodies in this instance may reflect the rapid turnover of serum IgE.

Use of a toluene monoisocyanate-human serum albumin test antigen as in this invention has permitted detection of tolyl-specific antibodies in TDI-sensitized workers. This finding supports an immunologic pathogenesis of TDI hypersensitivity. It is anticipated that this antigen will prove useful both in serological assays and in cutaneous testing for identification of sensitized individuals. By their removal from the exposure environment, it may be possible to prevent cutaneous or bronchial hypersensitivity reactions to TDI. In any event, the antigen and test method here disclosed makes it possible for the first time effectively to determine those persons who are sensitive to TDI.

In the foregoing specification we have set out certain preferred practices and embodiments of our invention, however, it will be understood that this invention may be otherwise practiced within the scope of the following claims.

We claim:

1. An antigen for detection of a selected diisocyanate comprising the reaction product of a protein and a monoisocyanate derivative of said selected diisocyanate.

2. An antigen as claimed in claim 1 wherein the selected diisocyanate is tolyl diisocyanate and the monoisocyanate derivative is p-tolyl isocyanate.

3. An antigen as claimed in claim 1 or 2 wherein the protein is human serum albumin.

4. An antigen as claimed in claim 1 wherein the selected diisocyanate is hexamethylene diisocyanate and the monoisocyanate derivative is hexyl isocyanate.

5. An antigen as claimed in claim 1 wherein the selected diisocyanate is diphenyl methane diisocyanate and the monoisocyanate derivative is diphenyl methane-4-isocyanate.

6. An antigen as claimed in claim 1 wherein the selected diisocyanate is isophorone diisocyanate and the monoisocyanate derivative is isophoronisocyanate.

7. An antigen as claimed in claim 1 wherein the selected diisocyanate is naphthylene diisocyanate and the monoisocyanate derivative is naphthylene isocyanate.

8. An antigen as claimed in claim 4, or 5 or 6 or 7 wherein the protein is human serum albumin.

9. A serological diagnostic test for a selected diisocyanate comprising the steps of:
 (a) preparing an antigen of said selected diisocyanate by reacting a protein with a monoisocyanate derivative of said selected diisocyanate;
 (b) adding said antigen to a paper disc activated with a coupling agent;
 (c) buffering said disc with an incubation buffer;
 (d) adding serum from a test subject to said buffered disc;
 (e) incubating said serum and disc with anti-IgE-$^{125}$I; and
 (f) counting said disc in scintillation fluid using a scintillation spectrometer.

10. A serological diagnostic test as claimed in claim 9 wherein the selected diisocyanate is tolyl diisocyanate, the monoisocyanate derivative is p-tolyl isocyanate, and the protein is human serum albumin.

11. A method of preparing an antigen for tolyl diisocyanate comprising the step of reacting p-tolyl isocyanate with a protein in buffered solution at about pH 9.

12. A method of preparing an antigen for tolyl diisocyanate as claimed in claim 11 wherein the protein is human serum albumin.

* * * * *

UNITED STATES PATENT AND TRADEMARK OFFICE
CERTIFICATE OF CORRECTION

PATENT NO. : 4,208,399

DATED : June 17, 1980

INVENTOR(S) : MERYL H. KAROL and YVES C. ALARIE

It is certified that error appears in the above-identified patent and that said Letters Patent are hereby corrected as shown below:

Column 4, line 1, "-0.5" should read -- -0.05 --.

Column 4, line 12, "11,400" should be --11,440--.

Column 4, line 55, "L" at the end of the line should be deleted.

Signed and Sealed this

Fourth Day of November 1980

[SEAL]

Attest:

SIDNEY A. DIAMOND

Attesting Officer

Commissioner of Patents and Trademarks